United States Patent
Takagi (10) Patent No.: US 11,430,120 B2
(45) Date of Patent: Aug. 30, 2022

(54) ULTRASOUND IMAGE EVALUATION APPARATUS, ULTRASOUND IMAGE EVALUATION METHOD, AND COMPUTER-READABLE NON-TRANSITORY RECORDING MEDIUM STORING ULTRASOUND IMAGE EVALUATION PROGRAM

(71) Applicant: Konica Minolta, Inc., Tokyo (JP)

(72) Inventor: Kazuya Takagi, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 262 days.

(21) Appl. No.: 16/566,516

(22) Filed: Sep. 10, 2019

(65) Prior Publication Data

US 2020/0104997 A1 Apr. 2, 2020

(30) Foreign Application Priority Data

Oct. 2, 2018 (JP) .............................. JP2018-187516

(51) Int. Cl.
G06T 7/00 (2017.01)
G06T 7/20 (2017.01)
A61B 8/08 (2006.01)

(52) U.S. Cl.
CPC .......... *G06T 7/0016* (2013.01); *A61B 8/5215* (2013.01); *G06T 7/20* (2013.01); *G06T 2207/10132* (2013.01); *G06T 2207/30004* (2013.01)

(58) Field of Classification Search
USPC ................................................ 382/128, 130
See application file for complete search history.

(56) References Cited

U.S. PATENT DOCUMENTS

| 8,187,186 B2 * | 5/2012 | Salgo ...................... A61B 8/08 600/438 |
| 8,211,021 B2 * | 7/2012 | Ichikawa ............... A61B 8/463 600/444 |
| 8,840,555 B2 * | 9/2014 | Miller ................. G01S 7/52042 600/438 |

(Continued)

FOREIGN PATENT DOCUMENTS

JP S63-77436 A 4/1988
JP 2008-079792 A 4/2008

(Continued)

OTHER PUBLICATIONS

Golemati et al., Ultrasound-Image Based Cardiovascular Tissue Motion Estimation, 2016 IEEE 1937-3333 vol. 9, pp. 208-2015 (Year: 2016).*

(Continued)

*Primary Examiner* — Ishrat I Sherali
(74) *Attorney, Agent, or Firm* — Lucas & Mercanti, LLP (57) ABSTRACT

An ultrasound image evaluation apparatus includes: an image obtaining section that obtains a first ultrasound image generated based on ultrasounds, and a second ultrasound image generated before the first ultrasound image; an evaluation section that evaluates a distribution of motions at a part in the first ultrasound image, and a corresponding part of tissue in the second ultrasound image; and an output control section that performs control of outputting an evaluation result of the evaluation section.

22 Claims, 8 Drawing Sheets

(56) References Cited

U.S. PATENT DOCUMENTS

| | | | |
|---|---|---|---|
| 9,119,557 B2* | 9/2015 | Masui | A61B 8/08 |
| 9,508,154 B2* | 11/2016 | Lee | G06T 19/00 |
| 11,138,735 B2* | 10/2021 | Haratake | A61B 6/032 |
| 2003/0083578 A1* | 5/2003 | Abe | A61B 8/485 |
| | | | 600/447 |
| 2007/0073145 A1* | 3/2007 | Fan | G01S 7/52065 |
| | | | 600/437 |
| 2008/0009699 A1* | 1/2008 | Sakas | G06T 7/33 |
| | | | 600/407 |
| 2008/0077011 A1* | 3/2008 | Azuma | G06T 7/215 |
| | | | 600/443 |
| 2008/0294048 A1* | 11/2008 | Salgo | A61B 8/08 |
| | | | 600/450 |
| 2011/0245673 A1* | 10/2011 | Kamiyama | G01S 7/52071 |
| | | | 600/443 |
| 2012/0116219 A1* | 5/2012 | Miller | A61B 8/485 |
| | | | 600/438 |
| 2015/0272547 A1* | 10/2015 | Freiburger | A61B 8/54 |
| | | | 600/438 |
| 2015/0302604 A1* | 10/2015 | Lee | G06T 19/00 |
| | | | 345/424 |

FOREIGN PATENT DOCUMENTS

| | | |
|---|---|---|
| JP | 2013-118984 A | 6/2013 |
| JP | 2013-188300 A | 9/2013 |

OTHER PUBLICATIONS

Kruizinga et al., Measuring Sub-micrometer Displacement Vectors Using High-Frame-Rate Ultrasound Imaging, 2015, IEEE 08835-3010 vol. 62 No. 10. pp. 1733-1744. (Year: 2015).*

Zhou et al., A Motion Estimation Refinement Framework for Real-Time Tissue Axial Strain Estimation With Freehand Ultrasound, 2010 IEEE 0885-3010, vol. 57, No. 9, pp. 1943-1951. (Year: 2010).*

Yuh-Hwan et al. Motion Tracking on Elbow Tissue from Ultrasonic Image Sequence for Patients with Lateral Epicondylitis, IEEE 1-4244-0788-5/07, pp. 95-98. (Year: 2007).*

Revell et al., Computer Vision Elastography: Speckle Adaptive Motion Estimation for Elastography Using Ultrasound sequence, 2005 IEEE 0278-0062, IEEE Transaction on Medical Imaging, vol. 24, No. 6, pp. 755-766 (Year: 2005).*

Lai et al., A Novel Adhesion Index for Verifying the Extent of Adhesion for the Extensor Digitorum Communis in Patients with Metacarpal Fractures, Sci Rep.2016;6:31102., Published online Aug. 5, 2016, doi:10.1038/srep31102, PMID: PMC4974625, PMID 27492808, pp. 1-9. (Year: 2016).*

Hermawan et al., Visualization of Shoulder Ligaments Motion by Ultrasound Speckle Tracking Method, 2020 IEEE 978-1-7281-1990-8/20, pp. 2084-2087. (Year: 2020).*

JPO, Office Action for the corresponding Japanese patent application No. 2018-187516, dated Jul. 19, 2022, with English translation.

* cited by examiner

100 # ULTRASOUND IMAGE EVALUATION APPARATUS, ULTRASOUND IMAGE EVALUATION METHOD, AND COMPUTER-READABLE NON-TRANSITORY RECORDING MEDIUM STORING ULTRASOUND IMAGE EVALUATION PROGRAM

CROSS REFERENCE TO RELATED APPLICATIONS

The entire disclosure of Japanese Patent Application No. 2018-187516 filed on Oct. 2, 2018 is incorporated herein by reference in its entirety.

BACKGROUND

Technological Field

The present invention relates to an ultrasound image evaluation apparatus, an ultrasound image evaluation method, and a computer-readable non-transitory recording medium storing an ultrasound image evaluation program.

Description of Related Art

An ultrasound diagnostic apparatus emits ultrasounds generated from an oscillating element internally included in an ultrasound probe, receives a reflection echo generated by a difference in acoustic impedance of tissue, and collects biological information (for example, see Japanese Patent Application Laid-Open No. S63-77436). According to an ultrasound diagnostic apparatus in recent years that can electronically control an ultrasound transmission and reception direction, and an ultrasound focused point, by controlling drive signals to be supplied to multiple oscillating elements, and delay times of received signals obtained from the oscillating elements, the inside of a body can be observed in real time in a non-invasive manner through images, and the apparatus is widely used for shape diagnosis and functional diagnosis of living organs.

Incidentally, orthopedics, rehabilitation and the like have cases of observing tissue adhesions in order to verify treatment effects. The observation is performed, for example, by moving the affected site (muscles and tendons) and visually identifying movement displayed on the ultrasound diagnostic apparatus.

Since such observation of the motion of muscles, tendons and the like using the conventional ultrasound diagnostic apparatus is visually performed, quantitative grasping cannot be made. Accordingly, conventionally, while an ultrasound probe (probe) is brought into contact with the body surface and the tissue is moved, determination is performed on the basis of subjective verification results (for example, presence or absence of adhesions, and the degrees of adhesions). That is, there is a problem of lacking quantitativity for evaluating tissue adhesions.

SUMMARY

An object of the present invention is to provide an ultrasound image evaluation apparatus, an ultrasound image evaluation method, and a computer-readable non-transitory recording medium storing an ultrasound image evaluation program that can quantitatively measure tissue adhesions.

To achieve at least one of the abovementioned objects, according to an aspect of the present invention, an ultrasound image evaluator reflecting one aspect of the present invention comprises: an image obtainer that obtains a first ultrasound image generated based on ultrasounds, and a second ultrasound image generated before the first ultrasound image; an evaluator that evaluates a distribution of motions at a part of tissue in the first ultrasound image, and a corresponding part of the tissue in the second ultrasound image; and an output controller that performs control of outputting an evaluation result of the evaluator.

To achieve at least one of the abovementioned objects, according to an aspect of the present invention, an ultrasound image evaluation method reflecting one aspect of the present invention comprises: obtaining a first ultrasound image generated based on ultrasounds, and a second ultrasound image generated before the first ultrasound image; evaluating a distribution of motions at a part of tissue in the first ultrasound image, and a corresponding part of the tissue in the second ultrasound image; and outputting an evaluation result.

To achieve at least one of the abovementioned objects, according to an aspect of the present invention, a computer-readable non-transitory recording medium reflecting one aspect of the present invention is a medium storing an ultrasound image evaluation program for causing a computer to execute: a process of obtaining a first ultrasound image generated based on ultrasounds, and a second ultrasound image generated before the first ultrasound image; a process of evaluating a distribution of motions at a part of tissue in the first ultrasound image, and a corresponding part of the tissue in the second ultrasound image; and a process of outputting an evaluation result.

BRIEF DESCRIPTION OF DRAWINGS

The advantages and features provided by one or more embodiments of the invention will become more fully understood from the detailed description given hereinbelow and the appended drawings which are given by way of illustration only, and thus are not intended as a definition of the limits of the present invention:

FIGS. 4A and 4B depict another display mode of an ultrasound image, an evaluation region and the like;

DETAILED DESCRIPTION OF EMBODIMENTS

Hereinafter, one or more embodiments of the present invention will be described with reference to the drawings. However, the scope of the invention is not limited to the disclosed embodiments.

Figure 1:
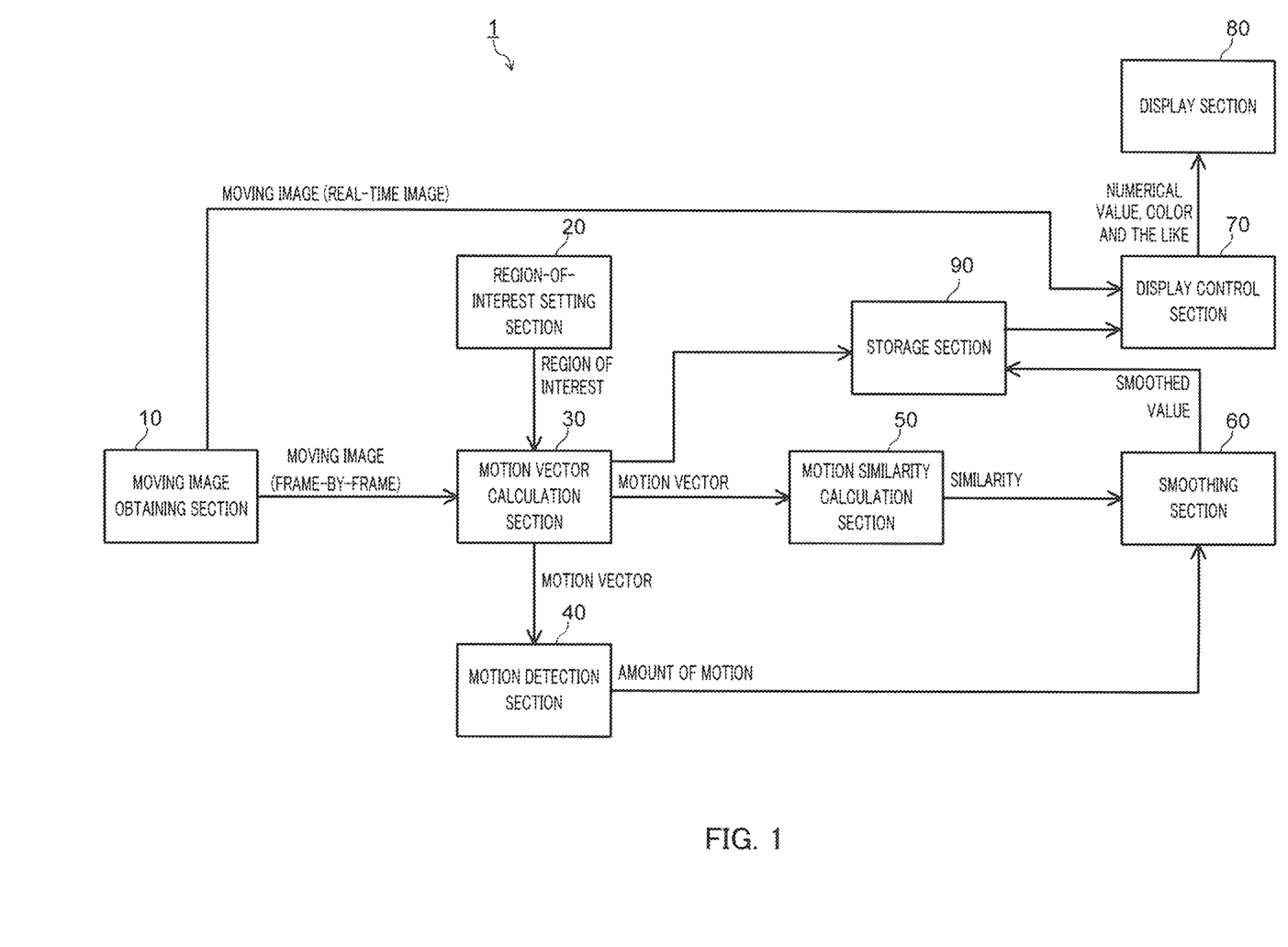
FIG. 1 is a block diagram schematically depicting an overall configuration of an ultrasound diagnostic apparatus according to this embodiment.

FIG. 1 is a block diagram depicting main functions of ultrasound diagnostic apparatus 1 according to this embodiment. For the sake of simplicity, in FIG. 1, illustration of publicly known parts, such as an ultrasound probe (hereinafter, simply called a probe) and an image generating unit, is omitted.

As shown in FIG. 1, ultrasound diagnostic apparatus 1 includes moving image obtaining section 10, region-of-interest setting section 20, motion vector calculation section 30, motion detection section 40, motion similarity calculation section 50, smoothing section 60, display control section 70, display section 80, and storage section 90.

Moving image obtaining section 10 has a function as an image obtaining section that obtains an ultrasound image generated based on ultrasounds emitted to an observation target.

In a specific example, moving image obtaining section 10 is connected to an image generating unit, not depicted, which generates a moving image (a set of frames) from ultrasound reflection echos received from a probe for transmitting and receiving ultrasounds to and from the observation target and obtains a moving image from such an image generating unit. Moving image obtaining section 10 receives a moving image from such an image generating unit. Moving image obtaining section 10 outputs the obtained moving image to motion vector calculation section 30 on a frame-by-frame basis according to an instruction of motion vector calculation section 30.

Moving image obtaining section 10 outputs the obtained moving image as a real-time image to display control section 70 according to an instruction from display control section 70.

Region-of-interest setting section 20 has a function of selecting a region to be measured among ultrasound images displayed on after-mentioned display section 80, and sets the region. In this embodiment, to measure the presence or absence and the degree of a tissue adhesion, region-of-interest setting section 20 plays a role of extracting and selecting a region (an affected site, an area around the affected site and the like) to be measured for the presence or absence and the degree of tissue adhesion from among all the regions of ultrasound images displayed on display section 80, on the basis of an operation by a user.

In a specific example, region-of-interest setting section 20 encircles a part of an ultrasound image displayed on display section 80 with a rectangular frame by an operation through an operation input section (trackball or the like), not depicted, thereby setting a region in such a frame as a region of interest.

Region-of-interest setting section 20 is an optional configuration element, and may be omitted. However, by providing region-of-interest setting section 20, a region of interest can be extracted by narrowing down, and be quantified. Accordingly, correctness of evaluating a taken image in the region of interest, that is, a tissue adhesion can be improved.

Motion vector calculation section 30 calculates the motion vector of each pixel or each small region (corresponding to "part" or "part of tissue" of the present invention) in the region of interest set (extracted) by region-of-interest setting section 20, from the ultrasound image output from moving image obtaining section 10. Specifically, motion vector calculation section 30 calculates the motion vector (the motion direction and the amount of motion) of each small region including a corresponding pixel or multiple pixels in the region of interest, in units of pixels or small regions, based on a publicly known tracking technique.

Motion vector calculation section 30 outputs the motion vectors detected from consecutive two frames as motion information, to motion detection section 40 and motion similarity calculation section 50 (see FIG. 1). After such an output process, motion vector calculation section 30 obtains an ultrasound image of the next one frame from moving image obtaining section 10, and calculates the motion vector of each pixel or each small region of the region of interest in an analogous manner.

Motion detection section 40 detects the amount of motion that is the maximum vector length among the lengths of motion vectors in units of pixels or small regions obtained from motion vector calculation section 30, and outputs the detected amount of motion to smoothing section 60.

Motion detection section 40 is an optional configuration element, and may be omitted. On the other hand, by providing motion detection section 40, an advantage is achieved that can exclude frames that should not be included as evaluation targets in principle, from analysis targets for smoothing section 60. Such a process of exclusion from analysis targets is described later.

Motion similarity calculation section 50 calculates the similarity of the motion vector in units of pixels or small regions obtained from motion vector calculation section 30 every time obtaining the motion information from motion vector calculation section 30, and outputs a calculation result as similarity information to smoothing section 60.

Smoothing section 60 analyzes the motion of the region of interest in a time series manner, based on the amount of motion obtained from motion detection section 40 and on pieces of similarity information successively obtained from motion similarity calculation section 50, performs overall evaluation, and outputs such an evaluation result to storage section 90. In this embodiment, smoothing section 60 smooths the similarity values successively obtained from motion similarity calculation section 50, and provides display control section 70 with a value obtained by the smoothing (smoothed value), through storage section 90.

Smoothing section 60 generates additional information on the ultrasound image to be displayed on display section 80, based on the aforementioned evaluation result (for example, an mean value or a weighted mean value), and outputs the generated additional information to storage section 90, which is a data storing medium, such as an HDD. Here, the additional information includes any or both of information indicating presence or absence of an adhesion, and information indicating the degree of the adhesion. In a specific example, various numerical values and a graph that pertain to the motion of an affected site, a color image to be superimposed on an ultrasound image or the like is generated as additional information, by smoothing section 60. The additional information may be displayed to be superimposed on the ultrasound image, or displayed outside of a display area for the ultrasound image.

Display control section 70 is connected to storage section 90, and performs a process of reading the ultrasound image and various pieces of additional information that are to be displayed on display section 80 from the storage section 90, and of displaying them on display section 80, as required. Furthermore, display control section 70 performs a process of displaying, on display section 80, a moving image (real-time image) supplied from moving image obtaining section 10, as required.

Display section 80 is connected to display control section 70, and displays, in real time, a moving image output from an image generating unit, not depicted, via display control section 70 and moving image obtaining section 10. Display section 80 displays an image of the additional information output from display control section 70, with the moving image.

In a specific example, a touch panel display is used as display section 80. In this case, the display can have both the functions of display section 80 and the operation input section (including region-of-interest setting section 20 described above).

Among the blocks described above, motion vector calculation section 30, motion detection section 40, motion similarity calculation section 50, and smoothing section 60 correspond to "evaluating section" of the present invention. Meanwhile, display control section 70 corresponds to "output control section" of the present invention. Motion vector calculation section 30, motion detection section 40, motion similarity calculation section 50, smoothing section 60, and display control section 70 may be made of a single processor (a CPU, an MPU or the like; this applies also to the description hereafter). Alternatively, these blocks may be appropriately made of a dedicated processor.

Storage section 90 may be disposed at a remote site. For example, a large capacity storage medium of a server (not depicted) that integrally manages data on many patients, hospitals and the like via a network may be used as storage section 90.

As described with reference to FIG. 3, a configuration may be adopted that displays, on display section 80, the motion vector (motion information) detected by motion vector calculation section 30, without use of similarity calculation by motion similarity calculation section 50 and the smoothing function by smoothing section 60. In this case, the calculation result of motion vector calculation section 30 may be directly output to storage section 90, or be output to storage section 90 via motion similarity calculation section 50 and smoothing section 60. In this case, motion vector calculation section 30 may generate additional information (a pattern of colored arrows or the like).

Figure 2A:
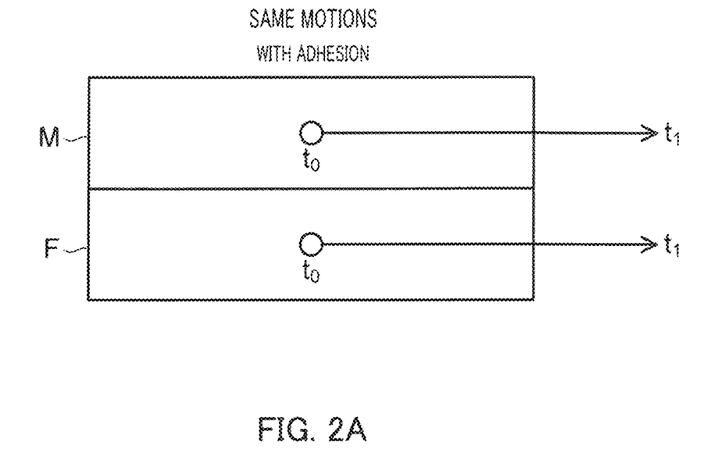
FIGS. 2A and 2B illustrate a difference in motion according to presence or absence of an adhesion between different pieces of tissue.
Figure 2B:
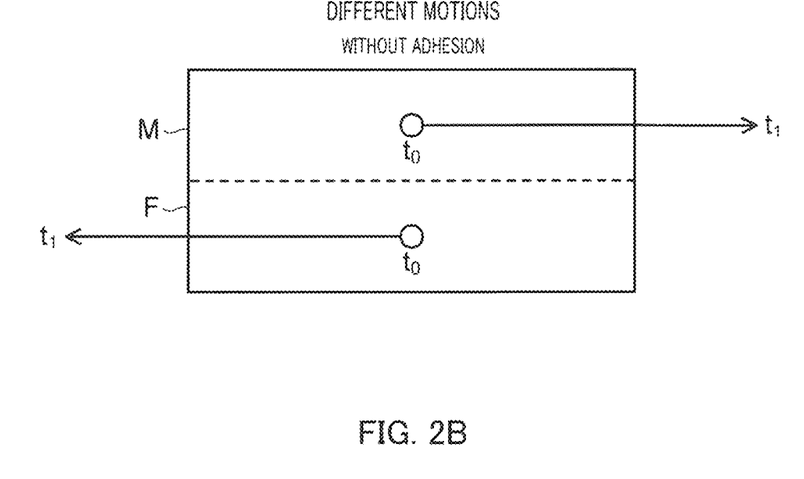

Next, referring to FIGS. 2A and 2B and thereafter, a method and the like that calculate the motion of tissue, the similarity of motion and the like from the obtained ultrasound images are described. FIGS. 2A and 2B depict the motions of different two types of tissue according to presence or absence of a tissue adhesion in a simplified manner for the sake of convenience of illustration. FIGS. 2A and 2B assume cases where two different pieces of tissue are taken in ultrasound images obtained by moving image obtaining section 10. In this example, fascia F is displayed below the region of interest, and muscle M is displayed above the region of interest.

In a specific example, when a motion of moving an affected site (for example, a motion of bending a wrist or a finger) is performed in a case where a tissue adhesion is checked based on ultrasound images, the following procedures are required.

Procedure 1: the probe is preliminarily fixed on the body surface (an arm in this embodiment).

Procedure 2: a measurement start button (not depicted) is turned ON to start to obtain an ultrasound image (see time $t_0$ in FIGS. 2A and 2B).

Procedure 3: in response to an instruction by a measurer, a motion for measurement (for example, a wrist bending motion) is started (see time $t_1$ in FIGS. 2A and 2B).

Here, in FIGS. 2A and 2B, sites indicated by white circles "○" indicate sites of fascia F and muscle M that face each other at time $t_0$. When a wrist or the like of a patient is moved in a predetermined direction for observation from this state, the motion directions of the facing sites are different between the case depicted in FIG. 2A and the case depicted in FIG. 2B.

Specifically, in the example depicted in FIG. 2A, the facing sites (white circles "○" in the diagram) of fascia F and muscle M between times $t_0$ to $t_1$ move in the same direction. Accordingly, it can be determined that fascia F and muscle M adhere to each other. On the contrary, in the example depicted in FIG. 2B, between $t_0$ to $t_1$, fascia F and muscle M move in different directions. Accordingly, it can be determined that fascia F and muscle M do not adhere to each other.

The examples depicted in FIGS. 2A and 2B assume cases of tracking the motion of a part (a point) of tissue over multiple frames from time $t_0$ to time $t_1$.

A current ultrasound diagnostic apparatus mainly uses a probe for obtaining a two-dimensional ultrasound image. Accordingly, there is a problem in that when tissue moves in a three-dimensional direction (depth direction), tracking cannot be performed.

In addition, observation is performed while tissue is being moved. Accordingly, there is a problem in that relative positional deviation between the probe and the body surface easily occurs. Consequently, for example, when ultrasound images of ten frames are obtained from time $t_0$ to time $t_1$ in the cases depicted in FIGS. 2A and 2B, a case can occur where a part of a living body that can be plotted with a white circle "○" in the first frame is not in the fifth to tenth frames and tracking cannot be performed accordingly.

As described above, it is difficult to continuously track the motion of tissue from the obtained ultrasound images. On the other hand, an apparatus capable of digitizing presence or absence and the degree of an adhesion is desired.

On the contrary, the present inventors performed various experiments while moving locomotor apparatuses, such as muscles and tendons. As a result, a knowledge can be obtained that even when tissue is moved in a complicated manner, substantially identical tissue can be grasped only in a short time period (typically, temporally consecutive two frames).

Based on such a knowledge, in this embodiment, presence or absence of an adhesion of pieces of tissue different from each other, the gliding ability, and the degree of adhesion can be quantitatively evaluated by measuring the motions of tissue closed in consecutive two frames that are temporally close to each other, and by averaging the measured motions in a time-series manner, without temporally tracking the motion of tissue in the living body over multiple frames.

To address the case of occurrence of three-dimensional motion of tissue described above, the present inventors achieve evaluation of the degree of adhesion by analyzing the motion in the region of interest, without tracking only a part (a point) of tissue in the living body.

Figure 3:
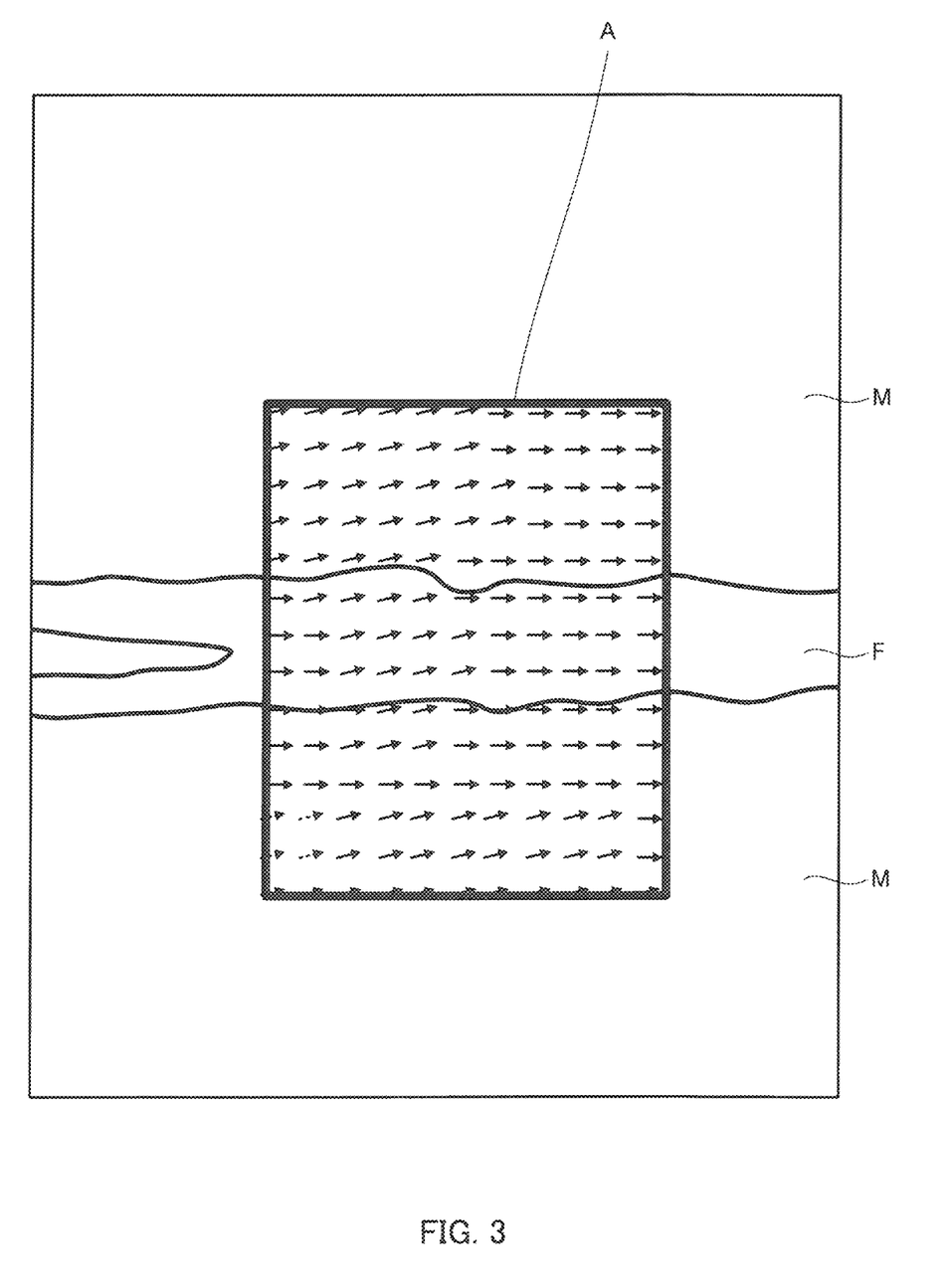
FIG. 3 schematically depicts a display mode of an ultrasound image, an evaluation region and the like in this embodiment.

FIG. 3 schematically depicts content displayed on display section 80 as a result of the present inventors' actually prototyping an apparatus according to this embodiment, imaging tissue, and performing measurement. In FIG. 3, fascia F is imaged at a substantially center in the vertical direction on the display screen of display section 80, and muscles M are imaged above and below fascia F (see also FIG. 4A). In the example depicted in FIG. 3, region of interest A is set so as to include multiple different pieces of tissue that are observation targets of presence or absence of an adhesion.

In this embodiment, display section 80 is a touch panel display. The user touches any point on the display screen, thereby allowing region of interest A to be automatically set; region of interest A has a predetermined shape (a rectangle in FIG. 3) including a region apart by a predetermined distance in the vertical and lateral directions from the touched point. The position, size and the like of automatically set region of interest A can be appropriately correct by an operation on the touch panel or an input operation through a trackball, not depicted, or the like.

Thus, determined region of interest A is fixed during execution of processes pertaining to evaluation in this apparatus (steps S10 to S80 in FIG. 6 and steps S100 to S220 in FIG. 7, described later). Meanwhile, since observation is performed while tissue is being moved, there is a possibility that positional deviation of region of interest A occurs. Accordingly, in a specific example, it is desirable that based on calculation results of motion vector calculation section 30 and motion detection section 40, a process of correcting the positional deviation of region of interest A be performed. The correction target of positional deviation is a motion having a low contribution to a motion in interest. For example, if there is an interest in motion in the horizontal direction, only positional deviation in the depth direction is corrected.

Furthermore, in FIG. 3, the motions of parts that are fascia F and muscles M in region of interest A calculated by motion vector calculation section 30 (each motion direction between consecutive two frames) are indicated by arrows. Specifically, motion vector calculation section 30 calculates the motion direction and the motion amount of each pixel or each small region about tissue in region of interest A between consecutive two frames output from moving image obtaining section 10, using the publicly known tracking technique (the optical flow technique in this example). In the case depicted in FIG. 3, fascia F and muscles M in region of interest A move in directions identical to each other (the right direction in this example). Accordingly, it can be determined that an adhesion occurs between these pieces of tissue.

FIG. 3 indicates the motion directions of parts in region of interest A calculated by motion vector calculation section 30 are indicated by arrows. Alternatively, a configuration may be adopted where the motion directions of the parts in region of interest A may be displayed as colored pixels. That is, a configuration may be adopted where display is performed with different colors according to the motion directions; for example, a site moving in the right direction is red pixels, a site moving in the left direction is blue pixels, a site moving in the upper right direction is orange pixels, a site moving in the lower right direction is yellow pixels, and a site stopping or moving in the depth direction is green pixels. Such display allows the motion of each part of tissue to be easily visually identified. Alternatively, a configuration may be adopted where the motion directions are indicated by colored arrows.

Figure 4A:
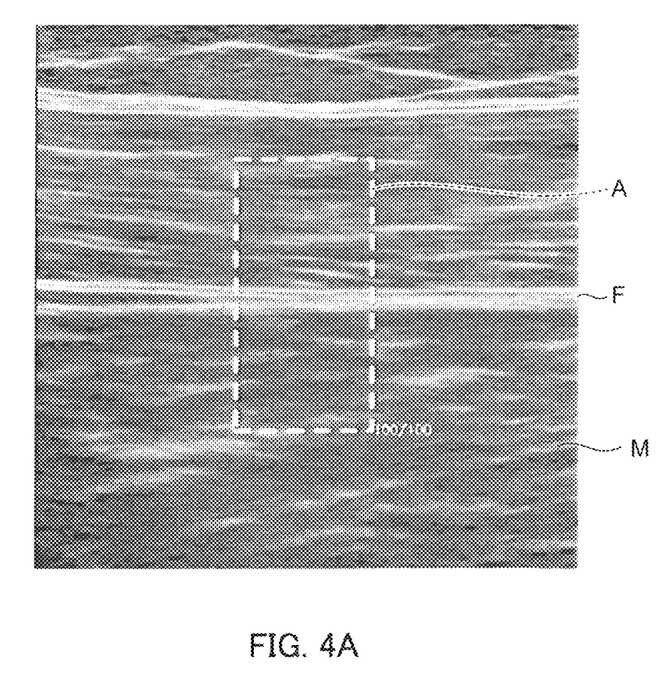
Figure 4B:
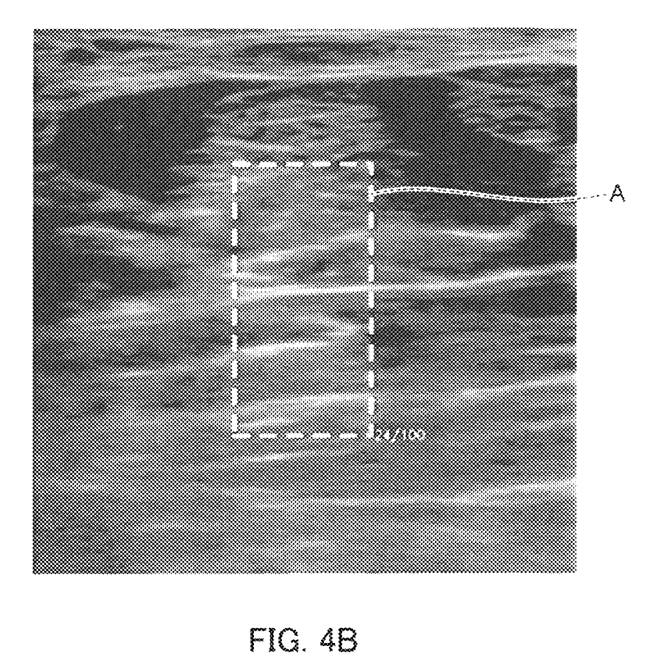

FIGS. 4A and 4B depict another display mode of an ultrasound image, an evaluation region and the like. A calculation result of the similarity by motion similarity calculation section 50, or a calculation result of smoothing section 60, described later, is displayed as additional information, at the right of region of interest A.

In this embodiment, motion similarity calculation section 50 calculates the mean vector (mvmean) of motions of pixels or small regions in region of interest A calculated by motion vector calculation section 30, according to following Expression 1.

[Expression 1]

$$\text{mvmean} = \Sigma_i \text{mv}_i/n \qquad \text{Expression (1)}$$

Expression (1) is an expression for obtaining the mean value of n motion vectors (the motion directions and the amounts of motions), in a case where the n motion vectors are in region of interest A.

Accordingly, motion similarity calculation section 50 calculates the cosine similarity (cossim) (or simply, the inner product value) between the mean vector calculated according to Expression (1) and the motion vector of each pixel or each small region in region of interest A, according to following Expression (2).

[Expression 2]

$$\cos sim = \frac{a_1 b_1 + a_2 b_2}{\sqrt{a_1^2 + a_2^2} \cdot \sqrt{b_1^2 + b_2^2}} \qquad \text{Expression (2)}$$

In Expression (2), vector a ($a_1$, $a_2$) is a motion vector (planar vector) of a pixel or a small region specified in region of interest A, and vector b ($b_1$, $b_2$) is the mean vector of n motion vectors calculated by Expression (1). Motion similarity calculation section 50 calculates the cosine similarity (cossim) of each of n motion vectors in region of interest A, according to Expression (2).

Furthermore, motion similarity calculation section 50 calculates the mean value (cossimmean) of the cosine similarities of the n motion vectors in region of interest A, according to following Expression (3), and outputs such a calculated value, as the similarity value, to smoothing section 60.

[Expression 3]

$$\text{cossimmean} = \Sigma_i \text{cossim}_i/n \qquad \text{Expression (3)}$$

The case depicted in FIG. 4A is a case corresponding or similar to the case described with reference to FIG. 3, and assumes that all the motion vectors of tissue detected in region of interest A (that is, the motion direction and the amount of motion of each sites of fascia F and muscles M) are aligned. In this case, 100/100 is displayed as the similarity.

On the other hand, FIG. 4B depicts the case where the motion vectors of tissue in region of interest A are not aligned. A low value (in this case 24/100) is displayed as the similarity.

As described above, the similarity of the distribution of motion vectors in region of interest A is displayed as a numerical value, which facilitates to semiquantitatively evaluate the motion of entire tissue imaged in region of interest A, in turn, presence or absence and the degree of an adhesion.

Motion vector calculation section 30 and motion similarity calculation section 50 calculate the motion vectors and their similarities in region of interest A using two frames consecutively output from moving image obtaining section 10, and each output calculated values. Here, the calculated values of motion vector calculation section 30 and motion similarity calculation section 50 can vary every time the frames are changed. Consequently, if such calculated values are displayed on display section 80, there is a possibility that visual identification by the user becomes difficult, and determination of the gliding ability becomes difficult.

Accordingly, in this embodiment, as depicted in FIG. 1, a configuration is adopted where smoothing section 60 is provided subsequent to motion similarity calculation section 50, and smoothing section 60 smooths the similarity values successively obtained from motion similarity calculation section 50, and displays the smoothed similarity value (see FIG. 4B and the like).

As for the display modes in FIGS. 4A and 4B, it is preferable to adopt a configuration where a predetermined one color is added to all the regions in region of interest A, according to the level of the calculated similarity (or the smoothed value, which is applied hereafter). In a specific example, in the case of FIG. 4A having a high similarity, region of interest A is displayed entirely in blue. In the case of FIG. 4B having a low similarity, region of interest A is displayed entirely in yellow.

In this embodiment, when the similarity increases (for example, 25/100 to 50/100), region of interest A is displayed entirely in green. When the similarity further increases (for example, 51/100 to 75/100), region of interest A is displayed entirely in purple. When the similarity is equal to or higher than 76/100, region of interest A is displayed entirely in blue as with FIG. 4A. Such display facilitates visual identification of presence or absence and the degree of an adhesion of tissue that is an observation target.

According to another additional or alternative example, motion similarity calculation section 50 may perform statistical analysis on the extent of the distribution of motion vectors, and output such an analytical value (a histogram or the like), as the similarity value, to smoothing section 60.

Figure 5:
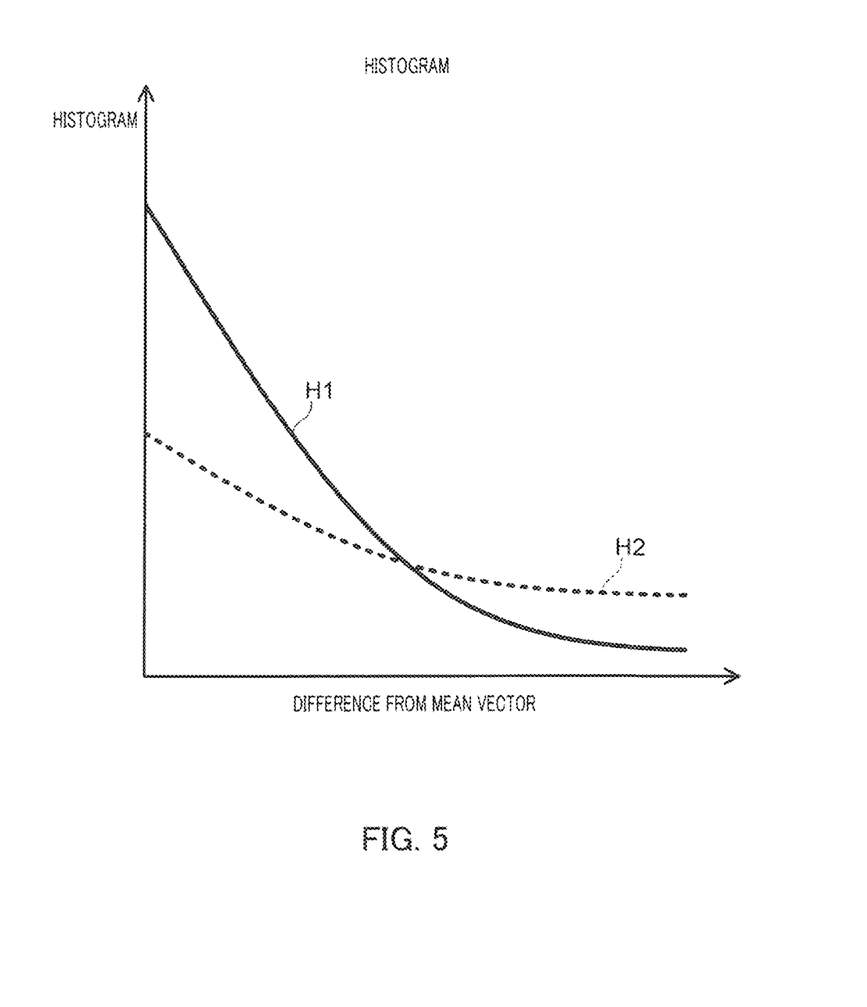
FIG. 5 schematically depicts histograms displayed as evaluation results.

FIG. 5 depicts histograms (H1 and H2) as statistical values of motion vectors. In the example of FIG. 5, the abscissa axis indicates the difference from the mean value (mean vector) of motion vectors (for example, the reciprocal of the aforementioned cosine similarity or inner product value), and the ordinate axis indicates the frequency. Comparison between the two histograms H1 and H2 depicted in FIG. 5 shows that histogram H1 has a higher the motion vector similarity than histogram H2 has.

That is, in histogram H1, the frequency of motion vectors having small differences from the mean vector (in other words, motions in directions identical or similar to each other) is higher, and the frequency of motion vectors having large differences from the mean vector (motions in different directions) is lower. On the other hand, histogram H2 has a frequency distribution inverted from that of histogram H1. Consequently, in view of "tissue adhesion degree," it is identified that the adhesion is weaker (the gliding ability is high) in histogram H2.

The display content described with reference to FIGS. 3 to 5 can be stored (temporarily stored or stored in long term) in storage section 90 automatically, or appropriately based on the user's setting operation. As required, the display content may be output on a sheet by a color printer or the like, not depicted.

Figure 6:
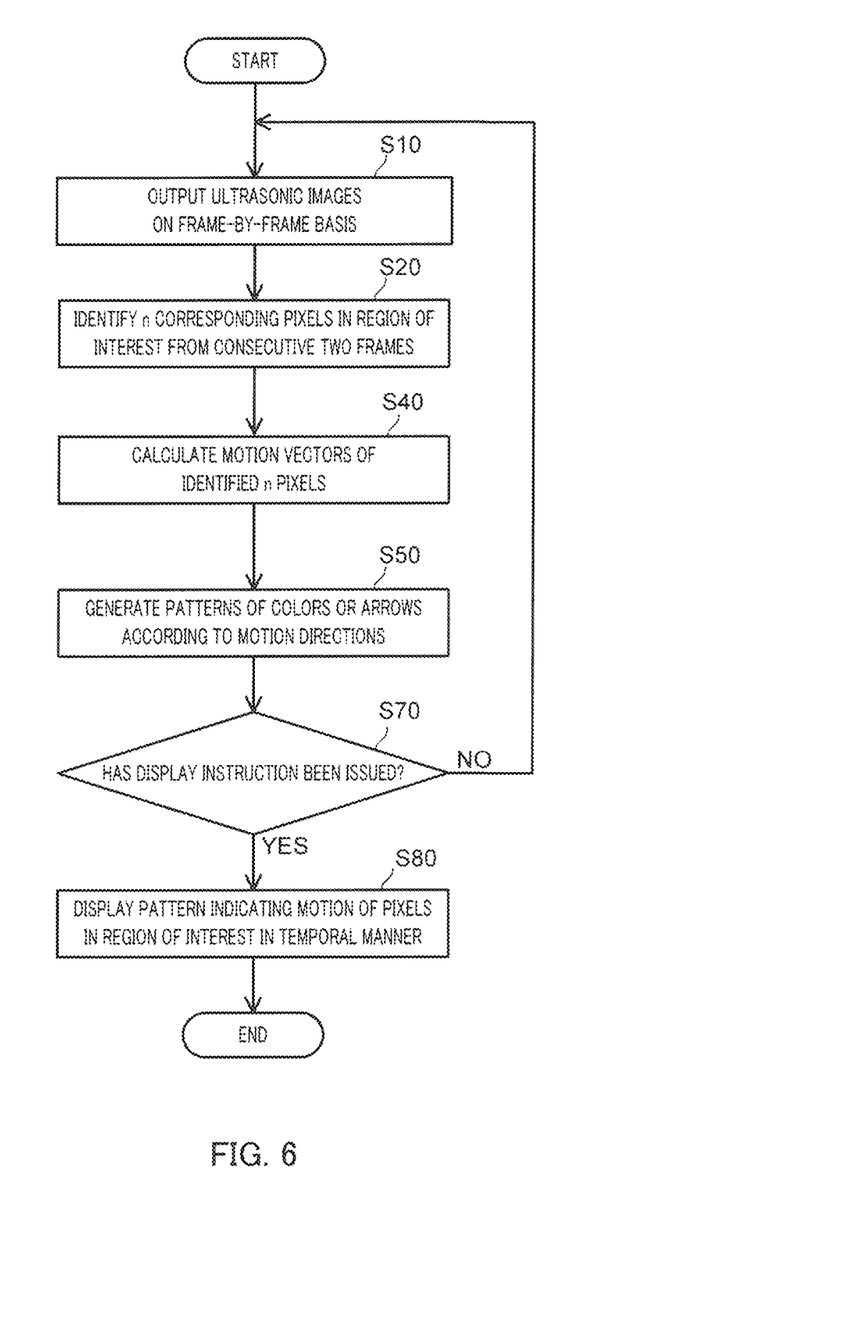
FIG. 6 a flowchart illustrating an example of processes of evaluating a distribution of motions in the ultrasound diagnostic apparatus of this embodiment.
Figure 7:
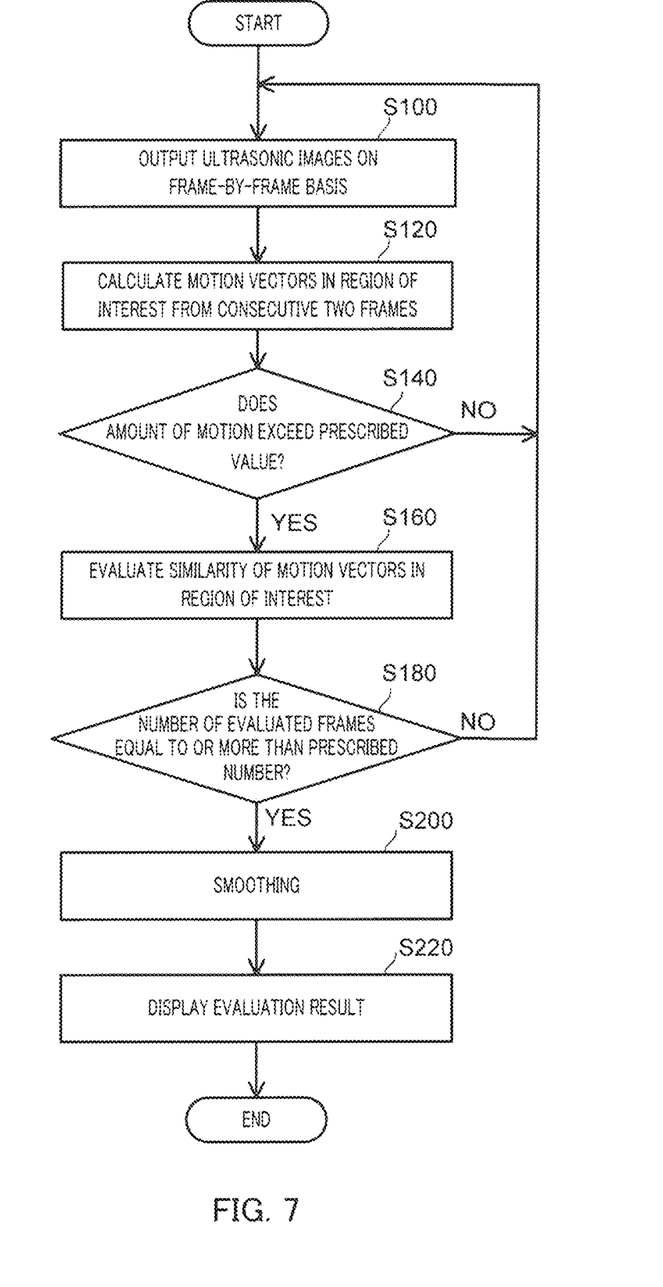
FIG. 7 is a flowchart depicting another example pertaining to processes of evaluating a distribution of motions in the ultrasound diagnostic apparatus of this embodiment.

Next, referring to FIGS. 6 and 7, a specific example of a process of evaluating the distribution of motions of tissue in ultrasound diagnostic apparatus 1 is described. Here, FIG. 6 is a processing flow corresponding to the display example described above with reference to FIG. 3. For the sake of simplicity, the configuration is assumed that the calculation result of motion vector calculation section 30 is directly output to storage section 90 (see FIG. 1). On the other hand, FIG. 7 is a processing flow in a case of using all the blocks depicted in FIG. 1. In a specific example, the processes depicted in FIGS. 6 and 7 are performed by a single processor in ultrasound diagnostic apparatus 1 reading and executing a program stored in a RAM.

Before starting the processes depicted in FIG. 6 or 7, the user brings (fixes) the probe, not depicted, of ultrasound diagnostic apparatus 1 into contact with the body surface, and causes display section 80 to display an ultrasound image of the tissue (fascia F and muscles M described above). To measure presence or absence or the like of an adhesion, a region of measurement target tissue (for example, the boundaries between fascia F and muscles M) in tissue displayed on display section 80 is designated as region of interest A, and display section 80 is caused to display the region. Furthermore, immediately before the tissue is moved, the user performs an input operation for starting measurement to thereby start the processes depicted in FIG. 6 or 7.

In step S10 in FIG. 6, moving image obtaining section 10 obtains a moving image (consecutive frames where still images are recorded) from the image generating unit described above, and outputs consecutive two frames of images (for the sake of convenience of description, called frame 1 and frame 2) to motion vector calculation section 30.

To filter noise and clarify a structure, a spatial compound technique of generating multiple images with varying ultrasound transmission and reception directions, and of combining these images is sometimes used, by a processing section (processor) in the image generating unit. That is, the processing section in the image generating unit performs the spatial compound processing by using an ultrasound image obtained by transmitting ultrasounds in a first direction, and an ultrasound image obtained by transmitting ultrasounds in a second direction different from the first direction.

Meanwhile, in a case where multiple images are combined into a single frame by the spatial compound processing, there is a possibility that the sensitivity of detecting motion vectors in motion vector calculation section 30 is lowered owing to a smoothing operation in in the temporal direction. Accordingly, in the case of using the spatial compound technique, "two frames" described above are images that are ultrasound images to which the spatial compound processing has not been applied by the processing section, that is, images having been obtained by transmission and reception of ultrasounds in the same direction (for example, in the right directions, or the left directions) but having not been subjected to the spatial compound. On the other hand, in a case without use of the spatial compound technique, temporally consecutive two frames are used.

Subsequently, as for the obtained two frames (1 and 2), motion vector calculation section 30 calculates the motion vectors in units of pixels in region of interest A according to a publicly known tracking technique (steps S20 and S40).

Specifically, in step S20, with respect to each pixel of tissue in region of interest A in frame 1, motion vector calculation section 30 detects n pixels (for example, pixels having similar luminances) of corresponding tissue in region of interest A in frame 2. Such a process associates a site of tissue in each small region in region of interest A between two frames.

In subsequent step S40, motion vector calculation section 30 calculates the motion vectors (the motion directions and the amounts of motion) of the detected n pixels on a pixel-by-pixel basis. Here, the motion direction is calculated from the directions and angle between the coordinate position of the pixel on the two-dimensional plane (XY coordinates) of frame 1, and the coordinate position of the corresponding pixel on the two-dimensional plane of frame 2. The amount of motion is calculated from the distance between the coordinate positions of the corresponding pixels in frames 1 and 2. Furthermore, motion vector calculation section 30 generates n patterns of colors or arrows according to the motion direction of each pixel, as an evaluation result (here, additional information to be superimposed on ultrasound images) (step S50). The generated additional information is output from motion vector calculation section 30 to storage section 90 and stored.

In step S70, display control section 70 monitors an input signal of the operation input section (the trackball or the like) described above, and determines whether a display instruction for the calculation result by motion vector calculation section 30 has been input or not. If it is determined that such a display instruction has not been input (NO in step S70), display control section 70 returns the processing to step S10, and repeats the processes in steps S10 to S70 described above. On the other hand, if it is determined that the display instruction has been input (YES in step S70), display control section 70 causes the processing to transition to step S80.

If the processing returns to step S10, moving image obtaining section 10 appropriately obtains a moving image (a new frame) from the image generating unit described above, and outputs the image of the next one frame (here, frame 3) to motion vector calculation section 30. As for the next two frames (obtained frame 3 and immediate previous frame 2), motion vector calculation section 30 calculates the motion vectors in units of pixels in region of interest A (steps S20 and S40).

In step S80, display control section 70 reads the additional information described above from storage section 90, and causes display section 80 to display the pattern of colors or arrows that indicates the motion of each of the pixels identified in region of interest A (see FIG. 3). At this time, display control section 70 displays the pattern of colors or arrows that indicates the motions of pixels in region of interest A in a time series manner (that is, in an order of frames) according to an operation of the operation input section (the trackball or the like).

By performing the processes described above, the motion of each small region in tissue in region of interest A is displayed in a manner of time-series of frames. Accordingly, presence or absence of an adhesion between pieces of tissue different from each other, and the degrees of the gliding ability and adhesion can be easily intuitively and quantitatively evaluated.

Next, referring to FIG. 7, a specific example of processes in the case of using each block in FIG. 1 is described.

Step S100 is analogous to step S10 illustrated in FIG. 6. That is, moving image obtaining section 10 obtains a moving image from the image generating unit, and outputs the images of consecutive two frames (frame 1 and frame 2) to motion vector calculation section 30 (step S100).

Subsequently, as for the obtained two frames (1 and 2), motion vector calculation section 30 calculates the motion vectors in units of pixels in region of interest A according to a publicly known tracking technique (step S120). Such a calculation process is analogous to the processes described with reference to steps S20 and S40 in FIG. 6. On the other hand, motion vector calculation section 30 outputs the calculated n motion vectors as motion information, to motion detection section 40 and motion similarity calculation section 50 (see FIG. 1). At this time, motion detection section 40 detects the motion vector having the largest size among the n motion vectors received from motion vector calculation section 30, and outputs it as the amount of motion to smoothing section 60.

In subsequent step S140, smoothing section 60 determines whether the amount of motion detected by motion detection section 40 exceeds a predetermined prescribed value or not. If smoothing section 60 determines that the amount of motion detected in motion detection section 40 exceeds the prescribed value (YES in step S140), the processing transitions to step S160.

On the other hand, if smoothing section 60 determines that such an amount of motion does not exceed the prescribed value (NO in step S140), the processing returns to step S100. Such a process excludes frames having an amount of motion that does not exceed the prescribed value (frame 1 and frame 2 in this example) from smoothing targets.

Such a process can evaluate only ultrasound images after start of operations for measurement, instead of adopting, as evaluation targets, ultrasound images in a state where tissue is in a stationary state or in a substantially not moving state (for example, states before and after measurement). Consequently, the reliability of the value calculated by the process of evaluation in a time series manner in smoothing section 60 (step S200), described later, is secured.

According to another processing example, if smoothing section 60 determines that the amount of motion detected in motion detection section 40 does not exceed the predetermined prescribed value (NO in step S140), smoothing section 60 may perform setting of reducing the weight of the frame having an amount that does not exceed the prescribed value and cause the processing to transition to step S160.

In step S160, a process of evaluating the similarities of motion vectors in region of interest A is executed by motion similarity calculation section 50 and smoothing section 60.

Specifically, in step S160, motion similarity calculation section 50 calculates the similarity of the motion vector in each pixel or each small region obtained from motion vector calculation section 30. Such a calculation method is as described above. Motion similarity calculation section 50 outputs the calculated value of similarity (cossimmean) to smoothing section 60.

In subsequent step S180, smoothing section 60 determines whether the number of calculated frames for similarity that have been obtained from motion similarity calculation section 50 and adopted as smoothing targets as described above reaches a predetermined prescribed number or not.

Here, if smoothing section 60 determines that the number reaches the prescribed number (YES in step S180), smoothing section 60 causes the processing to transition to step S200 and starts to calculate the evaluation value in a time series manner. In a specific example, smoothing section 60 performs a process of smoothing the similarity values obtained from motion similarity calculation section 50, and outputs the smoothed value to display control section 70.

On the other hand, if smoothing section 60 determines that the number does not reach the prescribed number (NO in step S180), smoothing section 60 temporarily stores the similarity value obtained from motion similarity calculation section 50 and returns the processing to step S100. That is, the smoothed value described above cannot be calculated only with a single similarity value obtained. Accordingly, when the number of adopted similarity values serving as smoothing targets reaches the predetermined number (for example, five), smoothing section 60 causes the processing to transition to step S200.

If the processing returns to step S100, moving image obtaining section 10 appropriately obtains a moving image (a new frame) from the image generating unit described above, and outputs the image of the next one frame (here, frame 3) to motion vector calculation section 30. In step S120, motion vector calculation section 30 obtains the motion vectors of the next two frames (obtained frame 3 and immediate previous frame 2). The processes in step S140 and thereafter are analogous to those described above. The description thereof is omitted.

Thus, when the processes in steps S100 to S180 are repeated and the number of similarity values serving as smoothing targets reaches the prescribed number (YES in step S180), smoothing section 60 causes the processing to transition to step S200. In step S200, smoothing section 60 smooths the similarity values obtained from motion similarity calculation section 50, and outputs the smoothed value as an evaluation result to display control section 70.

In subsequent step S220, display control section 70 generates additional information about the ultrasound image to be displayed on display section 80, on the basis of the evaluation result (smoothed value) obtained from smoothing section 60, and controls display section 80 to display the generated additional information with the ultrasound image.

In a specific example, as described with reference to FIGS. 4A and 4B, display control section 70 displays the obtained smoothed value at a predetermined position (on the right side of region of interest A in the examples of FIG. 4A), and displays all the regions in region of interest A in colors in conformity with the level of the smoothed value (similarity).

According to this embodiment that performs such processes, the gliding ability (adhesion) of tissue displayed as the ultrasound image can be quantitatively measured.

In this embodiment, in the display state on display section 80 in step S220 described above, the user can perform a process of storing data by operating the operation input section. In this case, display control section 70 makes a file of the ultrasound image of tissue and the evaluation result by each section (30 to 60), which are displayed on display section 80, and of the patient ID of the patient, and stores the file in storage section 90.

By performing such a process of storing data, for example, measurement results in various states, such as states before and after a treatment and rehabilitation are stored every time the state comes, and transition of the states of tissue can be grasped.

Figure 8:
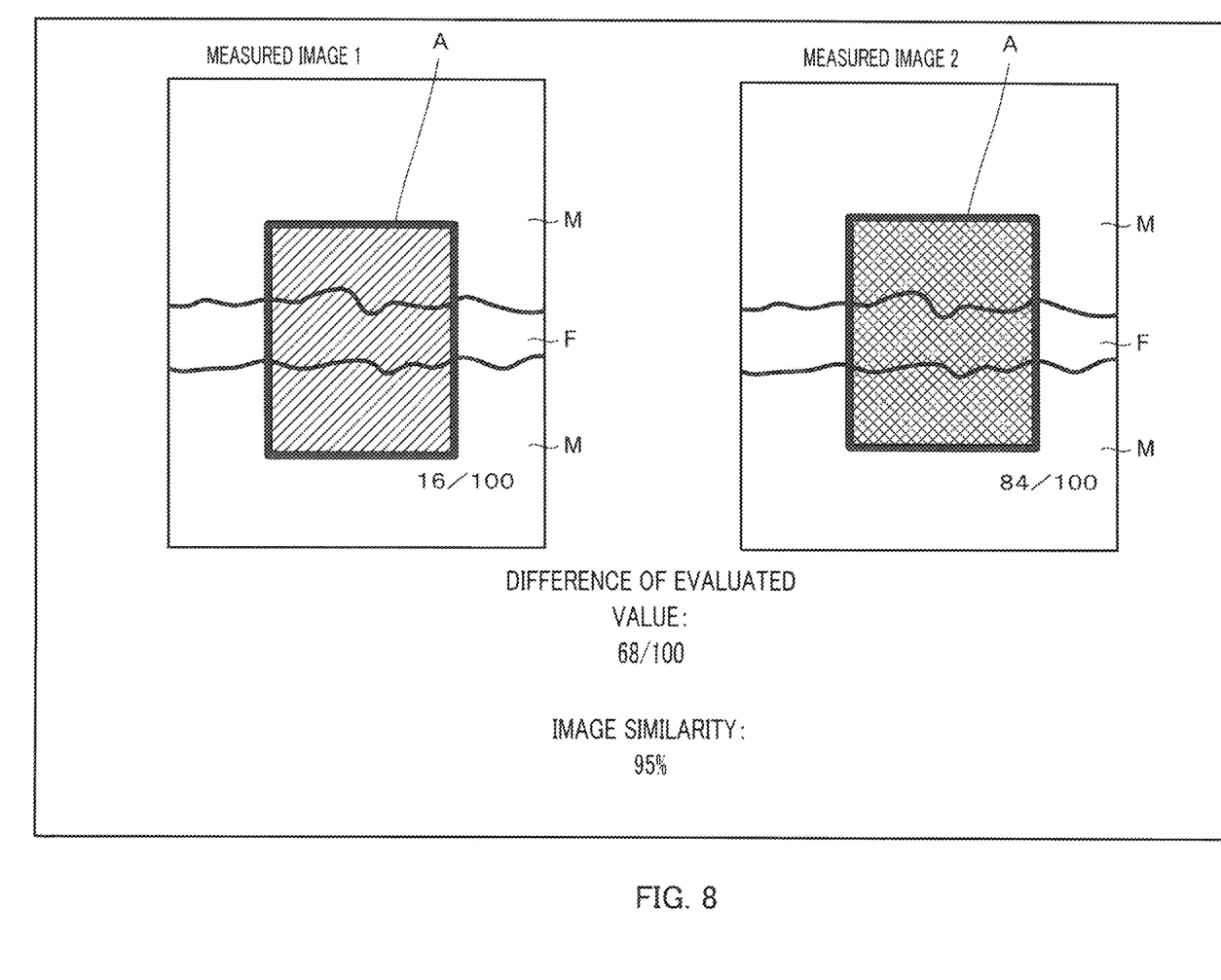
FIG. 8 depicts a display example in a case of displaying a first ultrasound image and the like generated previously, and a second ultrasound image and the like currently being measured, side by side, on a display section.

FIG. 8 depicts an example where a previous measurement result stored in storage section 90 is displayed as measured image 1 on the left side of display section 80, and a result of being measured this time (currently) is displayed as measured image 2 on the right side of display section 80, side by side. For example, in a case where an operation of inputting the patient ID is performed together before execution of step S100 described above, such display is performed by display control section 70 reading the file pertaining to measured image 1 associated with the patient ID from storage section 90.

In the example depicted in FIG. 8, an image measured before a treatment is displayed as measured image 1 on the left side of the display screen of display section 80, and an image measured after such a treatment is displayed as measured image 2 on the right side of the display screen.

At this time, display control section 70 reads the file pertaining to measured image 1 from storage section 90, and controls display section 80 to display the image of one frame used for measurement and the evaluation result (evaluation value or the like) on the left side of the display screen. Display control section 70 controls display section 80 to display a moving image (real-time image) input from moving image obtaining section 10, as measured image 2, side by side, on the right side of measured image 1.

By performing such processes, the user can easily align the probe in the same condition as that during measurement last time (measured image 1) (that is, the same position, the same angle and the like of tissue), with reference to the image of measured image 1 displayed on the left side of the display screen during measurement this time (measured image 2).

In addition, in this embodiment, to match the measurement condition between the measurement last time and the measurement this time as much as possible and improve reproducibility, a configuration is adopted that displays the image similarity between measured image 1 and measured image 2 (the similarity of images in region of interest A in this example) in a region between measured image 1 and measured image 2 on the display screen. Processes pertaining to such display are performed as described below, for example.

Before starting the processes depicted in FIG. 7 for measured image 2, the user adjusts the position of the probe and the like such that the image (real-time image) displayed as measured image 2 on the right side of the display screen of display section 80 can coincide with the image of measured image 1 displayed on the left side as much as possible, and sets region of interest A. At this time, display control section 70 inputs the image in region of interest A in measured image 2 and the image in region of interest A in measured image 1 into any block (motion similarity calculation section 50 in an example) constituting the evaluating section, and outputs an instruction for calculating the similarity between the two images. Here, motion similarity calculation section 50 calculates the value of similarity between the two images, by a publicly known pattern matching technique, for example. Display control section 70 controls display section 80 to display the similarity value calculated by motion similarity calculation section 50 at the lower center of the display screen, for example (see FIG. 8).

By performing such processes, the reproducibility of the imaging condition of the tissue in a case of performing ultrasound observation of tissue multiple times can be improved.

FIG. 8 depicts the state of display on display section 80 through execution of each process described with reference to FIG. 7 after the preprocess described above. Here, measured image 1 and measured image 2 have different evaluation values (smoothed values) calculated by smoothing section 60. According to such a difference, the colors added to region of interest A are different (such a difference in color is represented as a difference in hatching in FIG. 8).

In the example depicted in FIG. 8, the difference value (68/100 in this example) between the evaluation value (16/100) of measured image 1 and the evaluation value (84/100) of measured image 2 is displayed in a region between measured images 1 and 2 on the display screen. Processes pertaining to such display are performed as described below, for example.

That is, in step S200 described above, smoothing section 60 calculates the evaluation value (smoothed value) of measured image 2, and outputs such a calculated value (84/100 in this example) as the evaluation result of measured image 2 to display control section 70. Furthermore, smoothing section 60 calculates the difference between the calculated value (84/100) and the evaluation value (16/100) of measured image 1, and outputs the calculated value, as the difference between the evaluation values of measured images 1 and 2, to display control section 70.

According to the evaluation value and the value of the difference depicted in FIG. 8, it can be easily grasped that the gliding ability of tissue (tissue in region of interest A; this also applied hereafter) before the treatment (measured image 1), but the gliding ability of tissue is degraded and an adhesion occurs after the treatment (measured image 2). Subsequently, rehabilitation for restoring the gliding ability of tissue may be performed, then measurement may be performed again to generate and store measured image 3, and measured images 1 to 3, and their evaluation values and values of differences may be displayed on the display screen of display section 80.

In this embodiment described above, the configuration is adopted that smoothing section 60 selects frames of ultrasound images serving as targets to be evaluated by the evaluating section (motion vector calculation section 30 and the like), on the basis of the detection result of motion detection section 40.

Alternatively, another configuration may be adopted that allows each user to select frames of ultrasound images serving as targets to be evaluated by the evaluating section (hereinafter, called evaluation target frames).

In a specific example, the evaluation target frames may be frames generated after the user performs a predetermined operation and until immediately before the screen is largely switched. Here, "predetermined operation" may be, for example, any of various modes of operations that include pressing a predetermined button of the operation input section, pressing a start button on a touch panel, operating a trackball, and setting region of interest A. Furthermore, "screen is largely switched" is that the measurement target tissue in the ultrasound image displayed on display section 80 comes into a state of not being displayed. Such large switching (transition) of the screen can be determined from the detection result of motion detection section 40. Alternatively, with a certain type of probe to be used, the determination can be made from a detection signal of the probe.

According to another specific example, the evaluation target frames may be frames in a predetermined time range until immediately before the screen is largely switched. It is herein preferred that the user can freely preset "predetermined time range" according to a time period in which tissue is moved for measurement.

As described in detail, according to this embodiment, the configuration that evaluates the distribution of motions of tissue in consecutive two frames of obtained ultrasound images and outputs an evaluation result is provided, which can achieve quantitative measurement on tissue.

In the embodiment described above, the configuration has been described that uses, as an output control section, display control section 70 that controls display section 80, and displays information about the ultrasound images and the evaluation result on the display screen of display section 80. According to another alternative or additional example of the output control section, a configuration may be adopted that performs a control of printing (that is, printing out) the information about the ultrasound images and the evaluation result, or a control of outputting the evaluation result (a numerical value or the like) as a sound.

Although embodiments of the present invention have been described and illustrated in detail, the disclosed embodiments are made for purpose of illustration and example only and not limitation. The scope of the present invention should be interpreted by terms of the appended claims.

What is claimed is:

1. An ultrasound image evaluator, comprising:
an image obtainer that obtains a first ultrasound image generated based on ultrasounds, and a second ultrasound image generated before the first ultrasound image;
an evaluator that evaluates a distribution of motions in small regions of tissue in a region of interest between the first ultrasound image and the second ultrasound image, each of the small regions including one or more pixels of tissue in the region of interest, wherein the evaluator calculates an evaluation result based on a similarity of the motions in the small regions between the first ultrasound image and the second ultrasound image; and
an output controller that performs control of outputting the evaluation result of the evaluator and providing a visual identification of presence or absence and degree of an adhesion of the tissue.

2. The ultrasound image evaluator according to claim 1, wherein the evaluator evaluates the distribution of motions, based on motion directions of the small regions of the tissue.

3. The ultrasound image evaluator according to claim 2, wherein the evaluator evaluates the distribution of motions, based on directions of motions of a plurality of parts of the tissue in the first ultrasound image and the second ultrasound image.

4. The ultrasound image evaluator according to claim 2, wherein the evaluator generates a pattern of colors or arrows according to the motion directions, as the evaluation result.

5. The ultrasound image evaluator according to claim 1, wherein the evaluator generates, as the evaluation result, an evaluation value obtained by digitizing the distribution of motions, the evaluation value being displayed as the visual identification of presence or absence and degree of an adhesion of the tissue.

6. The ultrasound image evaluator according to claim 1, wherein the first ultrasound image and the second ultrasound image are two frames that are consecutive in a time-series manner.

7. The ultrasound image evaluator according to claim 1, further comprising
a processor that performs spatial compound processing by using an ultrasound image obtained by transmitting ultrasounds in a first direction, and an ultrasound image obtained by transmitting ultrasounds in a second direction different from the first direction,
wherein the first ultrasound image and the second ultrasound image are ultrasound images to which the spatial compound processing has not been applied by the processor.

8. The ultrasound image evaluator according to claim 5, wherein the evaluator generates the evaluation value, based on an extent of a distribution of motion vectors, when evaluating the distribution of motions.

9. The ultrasound image evaluator according to claim 1, wherein the evaluator evaluates distributions of motions of at least two pieces of tissue in a region of interest set in the ultrasound images.

10. The ultrasound image evaluator according to claim 1, wherein the output controller comprises a display controller that controls a display displaying the ultrasound images to display the ultrasound images, with the evaluation result of the evaluator being added to the ultrasound images as the visual identification of presence or absence and degree of an adhesion of the tissue.

11. The ultrasound image evaluator according to claim 10, wherein the display controller changes a color of region of interest in the ultrasound images displayed on the display, according to the evaluation result of the evaluator.

12. The ultrasound image evaluator according to claim 11, wherein the evaluator evaluates the distribution of motions, based on a first evaluation value for the ultrasound image obtained by the image obtainer in a first time period, and a second evaluation value for the ultrasound image obtained by the image obtainer in a second time period.

13. The ultrasound image evaluator according to claim 12, wherein the evaluator evaluates the distribution of motions, based on a difference between the first evaluation value and the second evaluation value.

14. The ultrasound image evaluator according to claim 12, wherein the display controller causes the display to display the first evaluation value and the corresponding ultrasound image, and the second evaluation value and the corresponding ultrasound image.

15. The ultrasound image evaluator according to claim 12, wherein the evaluator calculates an image similarity between the ultrasound image corresponding to the first evaluation value and the ultrasound image corresponding to the second evaluation value, and the display controller causes the display to display the calculated similarity.

16. The ultrasound image evaluator according to claim 12, further comprising a storage that stores the ultrasound images, and evaluation results of the evaluator that correspond to the respective ultrasound images,
wherein the display controller reads, from the storage, the first evaluation value and the corresponding ultrasound image, and displays the value and image on the display, before calculation of the second evaluation value.

17. The ultrasound image evaluator according to claim 1, wherein a target frame to be evaluated by the evaluator is set according to selection by a user.

18. The ultrasound image evaluator according to claim 15, wherein the evaluator determines whether to exclude a value of the similarity pertaining to frames according to amounts of motion of the ultrasound images or not.

19. The ultrasound image evaluator according to claim 1, wherein the image obtainer obtains the ultrasound images where two or more different types of tissue are taken.

20. An ultrasound image evaluation method, comprising:
obtaining a first ultrasound image generated based on ultrasounds, and a second ultrasound image generated before the first ultrasound image;
evaluating a distribution of motions in small regions of tissue in a region of interest between the first ultrasound image and in the second ultrasound image, each of the small regions including one or more pixels of tissue in the region of interest;
calculating an evaluation result based on a similarity of the motions in the small regions between the first ultrasound image and the second ultrasound image; and
outputting the evaluation result and providing a visual identification of presence or absence and degree of an adhesion of the tissue.

21. A computer-readable non-transitory recording medium storing an ultrasound image evaluation program for causing a computer to execute:
a process of obtaining a first ultrasound image generated based on ultrasounds, and a second ultrasound image generated before the first ultrasound image;
a process of evaluating a distribution of motions in small regions of tissue in a region of interest between the first ultrasound image and the second ultrasound image, each of the small regions including one or more pixels of tissue in the region of interest;
calculating an evaluation result based on a similarity of the motions in the respective small regions between the first ultrasound image and the second ultrasound image; and
a process of outputting the evaluation result and providing a visual identification of presence or absence and degree of an adhesion of the tissue.

22. The ultrasound image evaluator according to claim 1, wherein the evaluation result is based on a similarity between a motion vector of the unit including the one or more pixels and a mean value of motion vectors.

* * * * *